US006866841B2

(12) United States Patent
Grune

(10) Patent No.: US 6,866,841 B2
(45) Date of Patent: Mar. 15, 2005

(54) NON-ENDOCRINE DISRUPTING CYTOPROTECTIVE UV RADIATION RESISTANT SUBSTANCE

(75) Inventor: Guerry L. Grune, Virginia Beach, VA (US)

(73) Assignee: ePatentmanager.com, Va Beach, VA (US)

( * ) Notice: Subject to any disclaimer, the term of this patent is extended or adjusted under 35 U.S.C. 154(b) by 0 days.

(21) Appl. No.: 09/682,249

(22) Filed: Aug. 9, 2001

(65) Prior Publication Data

US 2003/0031634 A1 Feb. 13, 2003

(51) Int. Cl.[7] .............................. A61K 7/42; A61K 7/00; A61K 35/78
(52) U.S. Cl. ........................ 424/59; 424/401; 424/744
(58) Field of Search .......................... 424/401, 59, 744

(56) References Cited

U.S. PATENT DOCUMENTS

| | | | |
|---|---|---|---|
| 5,028,417 A | | 7/1991 | Bhat et al. |
| 5,188,831 A | | 2/1993 | Nicoll et al. |
| 5,340,567 A | | 8/1994 | Cole et al. |
| 5,356,811 A | | 10/1994 | Coats |
| 5,492,690 A | | 2/1996 | Bush |
| 5,498,406 A | | 3/1996 | Nearn et al. |
| 5,505,935 A | * | 4/1996 | Guerrero et al. ............... 424/59 |
| 5,547,659 A | | 8/1996 | Rinaldi et al. |
| 5,552,135 A | | 9/1996 | Cioca et al. |
| 5,565,591 A | | 10/1996 | Mitchnick et al. |
| 5,573,754 A | | 11/1996 | Kulkarni et al. |
| 5,573,755 A | | 11/1996 | Franklin et al. |
| 5,622,690 A | | 4/1997 | Potter et al. |
| 5,643,554 A | | 7/1997 | Menon et al. |
| 5,733,531 A | | 3/1998 | Mitchnick et al. |
| 5,741,924 A | | 4/1998 | Sovak et al. |
| 5,747,010 A | | 5/1998 | Geesin et al. |
| 5,747,011 A | | 5/1998 | Ross et al. |
| 5,770,183 A | | 6/1998 | Linares |
| 5,824,659 A | * | 10/1998 | Strickland et al. ............. 514/54 |
| 5,914,102 A | | 6/1999 | Fowler et al. |
| 5,916,542 A | | 6/1999 | Fossati |
| 5,945,090 A | | 8/1999 | Randall et al. |
| 5,965,518 A | * | 10/1999 | Nakatsu et al. ................. 512/1 |
| 5,972,362 A | * | 10/1999 | Wenker ...................... 424/407 |
| 5,980,871 A | * | 11/1999 | Lukenbach et al. ......... 106/436 |
| 6,015,548 A | * | 1/2000 | Siddiqui et al. ............... 424/59 |
| 6,042,813 A | | 3/2000 | Fowler |
| 6,048,517 A | | 4/2000 | Kaplan |
| 6,083,508 A | | 7/2000 | Avalos et al. |
| 6,099,825 A | | 8/2000 | McShane et al. |
| 6,284,234 B1 | | 9/2001 | Niemiec et al. |

FOREIGN PATENT DOCUMENTS

| | | |
|---|---|---|
| DE | 3642794 | 6/1987 |
| EP | 535372 A1 | 4/1993 |
| EP | 619999 A2 | 10/1994 |
| EP | 628303 A1 | 12/1994 |
| EP | 0834301 A1 | 4/1998 |
| JP | 1981-161881 | 5/1990 |
| WO | WO-06103 | 6/1990 |
| WO | WO 90/06103 | 6/1990 |
| WO | WO 93/11742 | 6/1993 |
| WO | WO-1993/11742 | 6/1993 |
| WO | WO 99/11236 | 3/1999 |
| WO | WO-1999/11236 | 3/1999 |

OTHER PUBLICATIONS

Margaret Schlumph,"In Vitro and in Vivo Estrogenicity of UV Screens", Envoronmental Health Perspectives, vol. 109, No. 3, Mar. 2001.
Michael Warhurst,"Introduction to Hormone Disrupting Chemicals" at <http://website.lineone.net/%7Emwarhurst>. Oct. 03, 2001, Internet.
Tioxide Co. Brochure published in Mar. 15, 1994 found at: http://www.psrc.usm.edu/macrog/coatings/tio2.htm> as of Oct. 11, 2001.
Margaret Schlumph, "Estrogen Active UV Screens", SOFW– Journal, vol.: 127, Jan. 07, 2001.
Marc S. Reisch, "Spotlight on Sunscreens", C & EN, Dec. 03, 2001.
Environmental Protection Agency Endocrine Disruptor Screening Program report to Congress, Aug. 2000, Internet: ttp://epa.gov/scipoly/oscpendo/index.htm, Aug. 07, 2002.
"Comments on 'In Vitro and in Vivo Estrogenicity of UV Screens'" Environmental Health Perspectives, vol. 109, No. 8, Aug. 2001.
"In Vitro and in Vivo Estrogenicity of UV Screens" Margaret Schlumph, Environmental Health Perspectives, vol. 109, No. 3, Mar. 2001.
Tioxide Co. Brochure published Mar. 15, 1994, found at: <http://www.psrc.usm.edu/macrog/coatings/tio2.htm> as of Oct. 11, 2001.
"Estrogen Active UV Screens" Margaret Schlumph, SOFW– Journal, 127, Jan. 7, 2001.
"Environmental Endocrine Disruptors" What Health Care Providers Should Know, Physicians for Social Responsibility. 2001.
"Spotlight on Sunscreens" Marc S. Reisch, C & EN, Dec. 3, 2001.
Environmental Protection Agency Endocrine Disruptor Screening Program Report to Congress Aug. 2000 <http://www.epa.gov/scipoly/oscpendo/index.htm> as of Aug. 7, 2002.

* cited by examiner

Primary Examiner—Michael G. Hartley
Assistant Examiner—Marina Lamm
(74) Attorney, Agent, or Firm—Guerry L. Grune

(57) ABSTRACT

Compositions for enhanced UV-protective agents that increase immuno-responsiveness by providing cytoprotective additives for mammalian skin while also providing avoidance from endocrine disrupting agents are described. A composition comprising:(a) at least one inorganic sun-blocking agent, (b) optionally at least one non-endocrine disrupting sunscreen agent, (c) at least one non-endocrine disrupting emollient with or mixtures thereof and (d) an optional oil component comprising a carrier oil, preferably an essential oil of a naturally occurring substance and a method of making this and other versions of similar compositions is detailed. The compositions areas shown to be capable of protecting skin and mammalian health from the harmful effects of radiation including ultraviolet light or sunlight by inhibiting the loss of skin immunocompetency and eliminating any endocrine disrupting agents normally utilized as sunscreen agents.

8 Claims, No Drawings

NON-ENDOCRINE DISRUPTING CYTOPROTECTIVE UV RADIATION RESISTANT SUBSTANCE

FIELD OF THE INVENTION

This invention relates to new and useful ultraviolet radiation protective agents that can be used as beneficial sunscreens and sun-blocks in various compositions or formulations. The compositions include enhanced protection and increased immuno-responsiveness by providing cytoprotective additives for mammalian skin while also providing avoidance from endocrine disrupting agents. It has been determined as of 2001, that sunscreen agents used in almost all currently marketed and sold ultraviolet protective compositions are essentially void of any cytoprotective agents and contain suspected or documented endocrine disruptive agents.

BACKGROUND OF THE INVENTION

Although a tan has long been considered a symbol indicative of good health and the ability to secure sufficient leisure time to enjoy many and numerous outdoor activities, it has become very evident that excessive exposure of the human skin to sunlight is harmful.

It is well documented that human skin and most likely most mammalian skin, is sensitive to sunlight and artificial light containing radiation of wavelengths between about 290 nanometers (nm) and 400 nm. Ultraviolet radiation of wavelengths between about 290 nm and 320 nm (UV-B region) has been known to rapidly produce damaging effects on the skin including reddening or erythema, edema, blistering or other skin eruptions in more severe cases. Prolonged or chronic exposure to radiation in this wavelength range has been associated with serious skin conditions such as actinic keratoses and carcinomas. In recent years, concern has also been expressed regarding ultraviolet radiation of wavelengths above 320 nm (UV-A region) and the adverse effects of such radiation on human skin. The radiation between 320 and 400 nm also contributes to the premature aging of the skin. In addition, recent studies indicate that chronic sun exposure limits the immunoresponse of the skin. There is some evidence that a tan will offer some protection against burning but that the tan is quite ineffectual against many other types of solar damage and there is no evidence that a tan increases immunoresponsive function in human skin.

Growing public awareness that the enjoyment of outdoor activities includes the need for adequate sun protection has led to an unprecedented growth in the area of sunscreen products. A very recent study by Margaret Schlumph from the Institute of Pharmacology and Toxicology at the University of Zurich, supports earlier health concerns regarding the use of endocrine disrupting organic substances in nearly all UV screening chemicals used in sunscreens. Additionally, the use of Aloe, or more specifically aloe barbadensis Miller has heretofore been known as a useful agent for the formulation of sunscreens as well as a substance that can both reduce UV damage to human skin that is inflamed and also promote healing. What was not well documented until recent publications and a subsequent U.S. Pat. No. 5,824,659 by Strickland and coworkers is that an extract found in all Aloe plants that is normally removed during carbon adsorptive processing, is capable of providing cyctoprotection to the mammalian skin. This extract boosts the immune system response of the skin, thereby significantly reducing the risk to various forms of skin cancer. There is strong evidence to suggest that this beneficial effect translates to skin in most mammals, thereby the present invention provides a possible preventative formulation for animals in zoos or other habitats where UV exposure could be hazardous to the animals' health.

It is therefore desirable to provide a UV protective product that has the following attributes: protection in both the UV-A and UV-B ultraviolet radiation ranges; maintenance of coverage, i.e., waterproof and perspiration proof; application and use convenience, i.e., ease of application, invisibility, non-staining and non-greasy; and freedom from irritation as a result of its ingredients, in particular, its active sunscreen ingredients should also be void of any known or suspected endocrine disrupters. Recent interest in this area includes some concerns over the irritancy and sensitization problems in addition to the endocrine disruptive nature that may occur in some individuals utilizing sunscreen products with high SPF values containing organic sunscreen agents. In addition, the UV protective product could also include known cytoprotective oligosaccharides from aloe barbadensis Miller preventing damage to the skin immune system caused by harmful UV radiation. "Cold-pressed" Aloe which contains the beneficial oligosaccharides and provides an emollient base for the UV protective formulation is possibly the best known choice as a cytoprotective agent that inhibits the loss of skin immunocompetency induced by ultraviolet radiation, as this agent is readily available and comparably inexpensive. Other such inhibitors are not yet well known but it is believed that amino-acids, vitamins or pro-vitamins, nucleo-derivatives, and vegetable extracts, wherein said amino-acids comprise tryptophan, histidine, phenylalanine, tyrosine, said vitamins and pro-vitamins comprise vitamin B6, vitamin A, vitamin E, tocopherols, betacarotene, bioflavonoids, nucleotides and polymers thereof, cascara, frangula, camomile, hyperic, calendula, elicriso, licorice or essential oils thereof all may have similar cytoprotective or immune boosting effects on mammalian skin.

One current measure of effectiveness of a sunscreen or sun-block product is indicated by its sun protection factor (SPF). The sun protection factor is the ratio of the amount of exposure (dose) required to produce a minimal erythema reaction in protected skin to the amount required to produce the same reaction in unprotected skin. The absolute dose differs for each human and for each mammal, and is largely dependent on genetic predisposition and ethnic origin of the human. If a human or other mammal would normally require ten-minute exposure to sunlight to develop a minimal erythema reaction, then using an SPF 15 sunscreen should allow for tolerance of up to 150 minutes of sunlight before developing a minimal erythema. Relatively recent public awareness of the problems of exposure to sunlight has led to a demand for sunscreen products with high SPF values, i.e., at or above SPF 8.

What has not been well considered in the sunscreen and cosmetics industry heretofore, is the possibility of enhancing the immuno-responsiveness of skin cells to UV light by the proper topical application such as described above by the use of extracts of aloe or similar naturally occurring substances. Such substances would preferably not be processed, but if the beneficial effects are not lost during processing, then either the processed or non-processed substance may be used.

A more complete rating mechanism than the SPF rating method is suggested here. The immuno-response rating system could be a simple 0–10 value, with 10 applying to a substance within the UV-protective composition that is most beneficial to boosting skin cell immune responsiveness to carcinoma, melanoma, etc. (for instance).

What has also not been well considered by the same industry is the effect that certain agents, recently determined to be endocrine disrupters, may have on certain mammals, particularly humans, regarding the immune system response to UV radiation. Endocrines are essentially excretions from organs or glands. The organs or glands continually function by discharging waste or at the least exchanging fluids from an inlet side to an outlet side. Any disruption in the natural behavior of an organ or gland could have a deleterious effect on the ability of that organ or gland to continue to function normally.

In a systems approach to health, the abnormal function of any organ or gland could lead to immune system disruptions (and immune system deficiencies) that may lead to serious health related complications. Changes in endocrine behavior has recently been linked to hormonal imbalances seen in young and especially adolescent or pubescent children, as well as in the global food chain where hermaphroditic insects and other animals have been discovered.

A UV-protective formulation or composition that may inhibit normal endocrine function(s) is at least undesirable, and at most a potential health threat to millions who continue to apply such a formulation or composition directly to their skin. Although the SPF value may be high, the potential for endocrine disruption may also be high and again this poses the possibility of another ranking system. In ranking potential endocrine disruption substances, again the 0–10 rating has appeal, with 0 being the desired criteria that a consumer would want to purchase to ensure consumption of a quality product that is also completely safe in terms of potential adverse health effects.

Therefore, as part of the present invention, a new rating system for UV-protective compositions is proposed that includes;

SPF value—greater than 15 desired
Immuno-responsiveness factor (IRF)-5 or higher desired (greater than 0)
Non-endocrine disrupter factor (NED)—0 desired Therefore the ultimate UV-protective formulation would safely block or screen UV light, enhance the immune responsiveness of the skin in the absence or presence of UV, and ensure the user that there is no endocrine disrupting substance present.

Ease of application and cosmetic appeal, on the other hand, are important in formulating sunscreen compositions. These characteristics rely on subjective evaluations such as visual and tactile impression by the user. Consumer research studies indicate that a sunscreen or sun-block formulation should rub in easily, leave the skin non-sticky and, above all should be invisible on the skin after application. Sunscreen compositions containing organic sunscreen agents have been found, in some cases, to irritate the skin. Additionally, recent studies have confirmed the suspicion that endocrine disrupting agents exist in currently available sunscreen formulations including; benzophenone-s, homosalate, 4-methylbenzylidene camphor, octyl methoxycinnamate, and octyl-dimethyl-PABA. All of these substances, in fact, made cancer cells grow more rapidly and three caused developmental effects in animals. Therefore a non-endocrine disrupting UV protective formulation should include the use of inorganic sun-block agents, such as titanium dioxide and zinc oxide. In addition the need for an acceptable emollient that reduces the negative affects associated with abrasive inorganics and that also includes the benefit of providing cytoprotection and healing of the skin is necessary. Allowing for the reduction of irritation or sensitization of the skin suggests that "cold-pressed" Aloe is a useful and necessary ingredient for such a UV-protective formulation.

Our review of the prior art in this field includes the following pertinent information;

For example, Japanese Patent Application No. 1981-161, 881, describes cosmetics containing 0.140% of ultrafine divided titanium oxide with a particle size of 10–30 nm which has been rendered hydrophobic. It indicates that when hydrophobically treated titanium dioxide with a particle size of 10–30 nm is blended into cosmetic base materials, it transmits visible light but reflects and scatters the harmful ultraviolet rays. It has been found that when these titanium dioxide compositions are utilized as a sunscreen agent in sunscreen compositions, it may result in the loss of one of the most desired properties of such compositions, i.e., invisibility.

U.S. Pat. No. 5,028,417, issued Jul. 2, 1991, describes sunscreen compositions containing microfine titanium dioxide. The particle size of the titanium dioxide is required to be less than 10 nm. It also states that other sunscreen agent can be utilized with the titanium dioxide.

U.S. Pat. No. 5,340,567, issued Aug. 23, 1994 describes a sunscreen composition comprising a synergistic combination of titanium dioxide having a particle size of less than about 35 nm and zinc oxide having a particle size of less than about 50 nm with titanium dioxide and zinc oxide being present at given ratios.

German Patent No. 3642794(1987) describes a cosmetic composition for preventing sunburn which contains 1–25% zinc oxide of a particle size of 70–300 microns. It further indicates that the composition may also contain titanium dioxide of a particle size of 30–70 microns. This composition is undesirably due to its unaesthetic whiteness characteristics at high SPF levels.

U.S. Pat. No. 5,188,831, issued Feb. 23, 1993, describes sunscreen compositions wherein the sunscreen effect is obtained from a blended of oil-dispersible ultrafine titanium dioxide and water dispersible titanium dioxide. However, the SPF level obtained is only of 10 with a total concentration of titanium dioxide of 5.0% w/w.

World Patent Application WO 90/06103, published Jun. 14, 1990, describes titanium dioxide sunscreen where the microfine titanium dioxide particles are coated with a phospholipid, either through the use of a powder mill or through the making of a dispersion in an oil phase containing the phospholipid with a high shear mixer. The phospholipid coated titanium dioxide is the incorporated into sunscreen compositions. A high efficiency is claimed: the data presented shows SPF values of up to 11 for a 3.75% titanium dioxide concentration and up to 25 for a for a 7.5% concentration of titanium dioxide. The use of high shear mixer or a powder mill is complicated and energy intensive process.

EP 535372 A1, published Apr. 7, 1993 describes a method of preparing sunscreens in which a dispersion of zinc oxide and/or titanium dioxide particles in an oil are formed by milling.

EP 619999 A2, published Oct. 19, 1994 describes an aqueous dispersion of particulate metallic oxide of particle size less than 200 nm mixed with an emulsifier and an oil phase and also an organic hydrophobic sunscreen to form an o/w emulsion. The resulting sun protection composition has a higher SPF than would be expected if there was only an additive effect. However, the titanium dioxide alone at 4% yielded a SPF of only 7 to about 11.

EP 628303, published Oct. 19, 1994 describes a process for preparing a sunscreen composition. It consists of mixing sunscreen particles of metallic oxide less than 200 nm dispersed in an oil with one or more emulsifier and/or organic sunscreens. The resulting sunscreen composition is claimed to have a SPF value considerably higher than expected. The high SPF is only obtained when a metallic oxide is blended with an organic sunscreen. In fact, when no organic sunscreen is used, the SPF value is only about 7.

WO 93/11742 describes sunscreen compositions comprising titanium dioxide and iron oxide of particle size less than 200 nm preferably coated with a phospholipid.

An article published in DCI in September 1992 by Tioxide Specialties Ltd. Describes ways of incorporating oil or water dispersions of titanium dioxide in emulsions. However, no data is given on the resulting SPF values.

An article published in Cosmetics and Toiletries, Vol. 107, October 1992, describes various ways of formulating with a physical sunblock. The discussion focuses on using titanium dioxide in a dispersion or using an emulsifier which is also an effective dispersing agent for titanium dioxide. It states that SPF's far above 20 can be achieved. However, no examples are given, nor does the article mention the specific sunscreen components or their composition.

A brochure published by the Tioxide Company on Mar. 15, 1994, discloses inorganic sunscreens of high SPF values obtained without the addition of any organic sunscreens. When measured, the SPF of the sunscreen compositions was indeed that described. However, when the titanium dioxide concentration was measured, it was at least twice what was claimed.

U.S. Pat. No. 5,498,406 describes sunscreen compositions in an oil-in-water emulsion containing both organic and inorganic sunscreens and comprising long chain (C2545) alcohols for stabilization of the emulsion. This composition relies predominately on the organic sunscreen actives. While the authors mention the use of stearic acid as a part of the oil in water composition, they teach against the use of stearic acid in stabilizing the titanium dioxide with C 22–45 alcohols.

U.S. Pat. No. 6,099,825 describes sunscreen having disappearing color which is extremely useful when combined with titanium dioxide or zinc oxide. It was unexpectedly found that although the inclusion of particulate pigments in a sunscreen emulsion can render the sunscreen visually colored as it is being spread onto the skin and that the coloration will substantially disappear when the sunscreen emulsion is rubbed into the skin.

U.S. Pat. No. 6,042,813 also describes sunscreen having disappearing color indicator. The sunscreen includes at least one active sunscreen agent, at least one emulsifier, sufficient amounts of water to create the colored emulsion, and at least one oil-soluble dye that imparts color to the emulsion.

U.S. Pat. No. 6,048,517, issued Apr. 11, 2000, describes low-cost sunscreen compositions with high SPF values of at least 40. The ingredients in the sunscreen include mixtures of homosalate, octyl salicylate, oxybenzone, octyl methoxycinnamate, or avobenzone.

U.S. Pat. No. 5,770,183, issued Jun. 23, 1998, describes an emulsion that contains a water phase and an oil phase that includes active sunscreen ingredients and skin conditioning agents. The sunscreen provides an SPF greater than 30, and the particle size in the oil phase averages 2.0 Microns, providing high levels of protection from the sun while using minimum amounts of active sunscreen agents.

U.S. Pat. No. 5,492,690, issued Feb. 20, 1996, describes a method for preventing skin damage by applying a substance that includes a benzolyacetate ester and seems to describe a potential non-endocrine disrupting benzoylacetate ester that would require testing prior to use in the present inventive composition(s).

U.S. Pat. No. 5,747,010, issued May 5, 1998, describes means and methods of protecting skin from the oxidative effects of UVA radiation using a substance that contains a lipophilic anti-oxidant. Such an anti-oxidant, if proven to be non-endocrine disruptive and not to interfere with the cytoprotective qualities of the present inventive composition(s) could also be useful and beneficial.

WO 99/11236 published first in Germany and then as a WO document dated Mar. 11, 1999, describes a transparent sunscreen gel that contains methylvinyl ether and maleic acid copolymers cross-linked with decadiene.

EP 0834301, published Mar. 8, 1998, describes compositions that include glutathione liposomes combined with at least one emulsifier and are topically applied to the skin to prevent the damaging effects of UV radiation.

U.S. Pat. No. 5,914,102, issued Jun. 22, 1999, describes an oil-in-water sunscreen emulsion comprised of at least one ultraviolet-absorbing organic compound and hydrophobically-treated silica particles. The concentration of the organic compounds is at least 30 times the concentration of the silica.

U.S. Pat. No. 5,916,542, issued Jun. 29, 1999, describes a mixture comprised of natural substances that effectively protect against skin damage caused by UVA and UVB light.

U.S. Pat. No. 5,945,090, issued Aug. 31, 1999, describes a high-SPF sunscreen comprised of an algae extract, aloe vera, and tapioca powder that protects against UVA and UVB light.

U.S. Pat. No. 5,980,871, issued Nov. 9, 1999 to Johnson and Johnson, and apparently licensed to Neutrogena, describes a sunscreen composition that includes inorganic sunscreen agents, such as titanium dioxide or zinc oxide, anionic emulsifiers, and an oil component. The composition allows for SPF greater than 10 with a titanium dioxide concentration of about 4%. This U.S. Pat. No. 5,980,871 further describes the method required to make the sunscreen.

This patented composition and method most closely resembles the present invention. There is no mention, however, of the use of any cytoprotective agents or the importance of providing only non-endocrine disruptive agents to the composition. In our review of commercially available products, this composition would appear to pose the least risk in terms of both short and longer-term health effects. The product itself, however, is somewhat undesirable as it leaves a very white appearance on the skin for long periods of time, is difficult to spread, and somewhat abrasive to sensitive skin.

Thus, in one possible embodiment, the present invention is directed toward a colored sunscreen or sun-block emulsion comprising: (a) at least one ultramarine pigment that imparts a color other than white to the emulsion with a titanium dioxide or zinc oxide or possibly fumed or fused silica or even silicon dioxide so that when the emulsion is rubbed into the skin, the color substantially disappears; (b) at least one sunscreen or sun-block active agent in an amount effective to protect skin against the actinic radiation of the sun; (c) no known or suspected endocrine disrupting organic substances; (d) a cytoprotective substance such as a glucose-rich mannose-containing oligosaccharide obtained from and used with aloe barbadensis Miller as the at least one emulsifier; and (e) sufficient water to form the other than a white colored emulsion.

The amount of the ultramarine pigment in the composition can range form about 0.5 to about 10 weight percent of the composition, preferably form about 1 to about 5 weight percent of the final formulation.

Optionally, the colored sunscreen emulsion can contain one or more additional ingredients, including emollients, waterproofing agents, dry-feel modifiers, insect repellants, antimicrobial preservatives and/or fragrances.

In another embodiment, the present invention is directed towards a method for protecting the skin against sunburn while increasing mammalian skin cell immunoresponse to cancerous skin cells while eliminating possible endocrine disruption response of human organs comprising topically applying the sunscreen formulation as described above to the skin.

An advantage of the present invention is that it provides a sunscreen or sub-block and a method for protecting against sunburn that enables the user to apply the sunscreen more completely and uniformly to the skin, thus providing more effective protection against skin damage and homogenously enhancing cytoprotection while eliminating endocrine disruptive organics, thus providing for long term health and safety in the presence of UV light.

Another advantage of the present invention is that it provides a sunscreen or sun-block with a color indicator which has a low fabric staining potential, and for which those stains that form can easily be removed from fabrics.

Still yet another advantage of the present invention is that it provides an optionally colored sunscreen or sun-block and a method for protecting against sunburn that is more enjoyable for human use because of the attractiveness and appealing nature of the color indicator.

For domesticated animals, the use of matching colors may also be appealing.

OBJECTS OF THE INVENTION

It is, therefore, an object of the present invention to provide improved sunscreen and sun-blocking agents and compositions. Review of the literature, and currently marketed compositions reveal that there exists an unnecessary potential risk to human health (or other mammals) with the current commercially available formulations on the worldwide market.

It is another object of the present invention to provide sunscreen or sun-block compositions containing sunscreen agents that overcome the disadvantages of heretofore available compositions and to provide non-endocrine disruptive, adequate, safe protection for mammalian skin while also enhancing the skin's immuno-responsiveness from cancerous or pre-cancerous skin cells in the presence of radiation such as UV light or sunlight.

Another object of this invention addresses the potential risks and disadvantages, provides a viable and economically attractive alternative to the present commercial market, and proposes a new and safer rating system to rank these products for the consumer.

These and other objects and features of the present invention will become readily apparent to one skilled in the art from the detailed description given hereinafter.

SUMMARY OF THE INVENTION

The foregoing objects and other features and advantages of the present invention are achieved by sunscreen and sun-blocking compositions containing inorganic sun-blocking agents or known non-endocrine disruptive sunscreen agents as the active ingredients. More particularly, the present invention relates to sun-blocking compositions containing titanium dioxide and, optionally, zinc oxide of preferred particle size ranges, and in preferred amounts and ratios. These sun-blocking agents together with specifically cold-pressed aloe that contains an oligosaccharide of molecular weight of approximately 1–5,000 daltons that is glucose rich and also contains mannose which inhibits the loss of skin immuno-competency form the basis of a novel protective UV formulation.

These specific compositions permit the use of much lower amounts of the sunscreen active ingredients than previously achievable while still achieving desired and very high SPF values for the compositions and without the unsightly whiteness which occurs in prior sunscreen compositions at concentrations above about 5%. In the sun-block compositions of this invention, considerably higher concentrations of titanium dioxide may also be used without incurring a whitening effect, e.g., even up to 15% with acceptable appearance, or possibly higher.

Furthermore, our invention does not rely upon the use of hydrophilic titanium dioxide preparations as required in the above noted patents, nor are energy intensive processes such as powder milling, nor are organic active sunscreens required for high efficacy.

The compositions of this invention are oil-in-water emulsions containing at least the following components:
(a) an inorganic sun-blocking agent and/or a non-endocrine disruptive sunscreen agent;
(b) a non-endocrine disrupting and cytoprotective emulsifier or mixtures thereof;
(c) an optional oil component comprising a carrier oil, preferably an essential oil any of which are also non-endocrine disruptive and;
(d) at least one emollient, where said emollient may be the cytoprotective emulsifier of (b) above.

The emollient is preferably aloe as it is "cold pressed" or an extract of aloe that is currently removed during normal processing and recovered by some means. The aloe or its extract may not provide sufficient emulsification based on the remaining ingredients of the composition.

The compositions of this invention provide formulations having an SPF of at least 10 with a concentration level of titanium dioxide of about 4%. The compositions of this invention exhibit extremely efficient uses of sun-block components, particularly titanium dioxide. The compositions of this invention therefore may be formulated so as to contain relatively smaller amounts of titanium dioxide than used heretofore at a given SPF level. Alternatively, higher levels of titanium dioxide or zinc oxide can be used if ultramarine pigments are added to the composition. These pigments are known to eliminate the whiteness and poor spreadability of currently available compositions. For the purposes of this invention, however, these pigments must be known to be non-endocrine disruptive as well as to not interfere with the cytoprotective influence of the oligosaccharide aloe extract.

Essentially, the compositions of this invention are easily made by simple mixing and provide an excellent dispersion of the inorganic based sunblock agent throughout the composition, thus ensuring even skin coverage. With the use of ultramarine pigments, after initial coloring effects, the compositions are substantially invisible upon application to the skin.

DETAILED DESCRIPTION OF THE INVENTION

The UV-protective compositions of this invention yield highly effective ultraviolet (UV) blocking capabilities. A given level of protection may be provided with a significantly lower concentration of titanium dioxide than previously obtained using commercially available powdered titanium dioxides. They do not require the unusual processing methods previously necessary to disperse the titanium dioxide into an oil, such as preparation of sub-batch mill bases, high shear mixing or milling, or applying such milling procedures to the final product formulation. A typical titanium dioxide sun-block composition of SPF 15 requires levels of titanium dioxide that impart a significant whitening effect to the skin; the compositions of this invention, minimize this disadvantage and are therefore economically viable to produce.

The composition of this invention are oil-in-water emulsions that are cosmetically superior to conventional inorganic preparations, including water-in-oil titanium dioxide-only formulations, at equivalent SPF ratings, due to the low levels of titanium dioxide or zinc oxide needed in the invention system. The compositions of this invention can be used for sun protection in daily wear or facial products as well as for recreational situations. Because of the efficiency of the system, the inventive formulations are significantly lower in cost than other sunscreen/sun-blocking systems.

There are several ingredients that contribute to the unexpectedly high efficiency of the compositions blocking of UV radiation. It has been found, however, that only one known UVA protector, butyl-methoxydibenzoylmethane has been shown to be benign regarding activity in cells or developmental effects on animals. Depending on the need for individual formulations based on the inventive concept herewithin, the use of this or other UVA protectors may be required. The formulation of this invention is intended to filter harmful UVA as well as harmful UVB radiation so that the skin is fully protected. As each mammal's immuno-response system and skin composition is different, the required amounts required for application to the skin will vary. In addition, the actual UV protective formulation will vary based on the environmental location, length of exposure, age, health and other factors involving individual mammals, such that the concentrations of non-endocrine disruptive UVA screens, UVB screens, inorganic pigments, and cytoprotective agents will vary.

The compositions of this invention may by necessity include one or more of a select group of anionic emulsifiers. In particular, salts of certain fatty acids are useful in the formulations of this invention, preferably salts of saturated fatty acids and/or salts of straight-chain fatty acids. Alkali metal salts, alkali earth metal salts and amine salts are more preferable for use in the compositions of this invention. For example, stearic acid and its salts are useful as emulsifiers in the compositions of this invention, while the use of isostearate salts tends to produce a composition which is not very efficient in the use of sun-block. Likewise, oleate salts are not useful as they are unsaturated and do not result in efficient sunscreen or sun-block compositons.

It is not yet known which, if any of these substances are endocrine disrupters or which if any may reverse or reduce the effect of cytoprotective substances to be used in the composition of the present invention. Any such anionic emulsifiers would have to be tested prior to addition to the composition of the present invention and are to be the subject of future research.

More particularly, the following anionic emulsifiers are useful in the compositions of this invention: sodium stearate, sodium lauryl sulfate, DEA cetyl phosphate, sodium dioctyl sulfosuccinate and the like. Most preferably, the emulsifier should be sodium stearate. While it is not fully understood why some salts of fatty acids result in an inventive composition, it is theorized that salts of straight-chain fatty acids, (the fatty acids having a relatively high melting point, above 70 C. or higher), are preferable due to their structure. For example, salts of branched or unsaturated fatty acids are most likely not acceptable for use in the compositions of this invention.

The anionic emulsifiers should be present in the compositions of this invention in an amount from about 0.01 to about 10%, more preferably 0.1 to about 7% and most preferably from about 0.5 to about 5%. There may be additional emulsifiers present in the compositions of this invention, such as nonionic emulsifiers known to those of ordinary skill in the art such as sorbitan esters and ethoxylated sorbitan esters, ethoxylated fatty acids, fatty alcohols and ethoxylated fatty alcohol's, fatty glyceride esters and ethoxylated fatty glyceride esters and the like. However, there may have to be at least one anionic emulsifier present in order to achieve the products of this invention. The fatty acid salt emulsifiers may be added to the composition as the salts, or the salt may be formed in situ. In all cases, these additives would only be present if they are found to be endocrine disruption free and non-deleterious to any inhibition of skin immuno-competency.

A carrier oil may also be required in the compositions of this invention. It may be selected from the group of essential oils or other known non-endocrine disrupter esters such as butylmethoxydibenzoylmethane.

Another possible carrier oil could be a C8 to C22 fatty alkyl (optionally polypropyleneoxy) polyethyleneoxy carboxylate ester, the ester having an alkyl group which has from on to twenty-two carbon atoms, optionally straight or branched or can contain a phenyl group. Most preferably, the carrier oil should be isopropyl PPG-2 isodeceth-7 carboxylate, such as Velsan D8P3 or other commercially available materials sold by Clariant under the Velsan trade name. Other similar structures include Hetester PHA available from Bernel. All such oils must be proven to be non-endocrine disrupters and to not interfere with the inhibition of skin immuno-competency.

Preferably, the carrier oil which is more preferably an essential oil, should be present in the composition in an amount of between about 0.1% and about 10%. More preferably, it should be present in the amount of between about 1% and about 5%. Most preferably, it should be present in the amount of between about 2% and about 3%.

For conventional UV-protection formulations, the oil phase should contain at least two materials, the carrier oil or essential oil and a conventional emollient known to those of ordinary skill in the art as useful in sunscreen products, such as mineral oils, ester oils, vegetable oils, silicones, synthetic emollients such as fatty acid esters and the like. For the present invention, the use of a cold pressed aloe barbadensis Miller is to be substituted as an emollient or can be used in combination with the oils or synthetic emollients that are proven to be non-endocrine disrupting as well as not interfering with augmenting the cytoprotective enhancing effects of the known effective oligosaccharide aloe extract. The emollient should be present in the formulation in a ratio to the carrier concentration of from about 1:1 to about 3:1, most preferably, about 2:1. The carrier oil and the emollient should compose from about 2% to about 20% of the total composition weight.

A third element which should be present in the compositions of this invention is an inorganic sun-block compound, such as titanium dioxide, zinc oxide or combinations thereof. Possible other inorganics include the use of fused or fumed silica or even silicon dioxide. Preferably, titanium dioxide should be used having a primary particle size from of less than about 300 nm in diameter. It should be present in the composition in the amount of from about 2% to about 25%. More preferably, it should be present in the amount of from about 2% to about 15%. Most preferably, it should be present in the amount of from about 3% to about 10%. The inorganic sun-block compound should be oil dispersible, and may be present with or without surface coating.

The ratio of titanium dioxide to the weight of the carrier oil and the emollient combined should be from about 0.3:1 to about 1:1. Most preferably, the ratio should be between about 0.5:1 and 2:3.

In the case where salts of fatty acids are used care should be taken to keep the pH of the compositions of this invention at a level above about 5, more preferably, above about 5.5. Maintaining the pH at this level will ensure that these anionic emulsifiers remain in the salt form, which is important in retaining the stability and efficacy of the composition.

Additionally, the usual elements of a modern sunscreen emulsion system may be necessary such as a polymeric thickener/stabilizer, one or more additional emollient oils, microbial preservations, waterproofing agents, antioxidants, fragrance, humectant, and of course the water vehicle may all utilized using careful selection or restraint based on the constraints of providing a non-endocrine disrupting immuno-enhancing composition.

The base formulation of this invention may also be used as carrier compositions for active topical agents having dermatological effects, including depigmentation agents, anti-aging ingredients, antifungal agents, antimicrobial agents, insect repellents and the like. For example, depigmentation agents can include magnesium ascorbyl phosphate or hydroquinone but only used in the final composition if these agents are shown not to be endocrine disrupters. Anti-aging agents can include retinoid compounds and alpha-hydroxy acids again only if In accordance with the two-vessel process, a water phase is prepared by measuring deionized water into a beaker and mixing. The elements of the water phase, including emulsifiers and humectants, chelators, thickeners, waterproofing agents, neutralizing agents and antioxidants should be added and the solution heated. If an anionic emulsifier is used it may be placed into the water phase or into the oil phase, depending upon the nature of the emulsifier. The oil phase is prepared separately in another vessel, including the anionic emulsifier, carrier oil, emollient and inorganic sunscreen agent. The two phases are then held at a relatively high temperature and mixed.

In the one-vessel process, the water and oil phases may be made in the same vessel, provided that the components are added in an appropriate order. For example, the water phase should be created first, adding water and optionally certain emulsifiers which are compatible with the water phase to the vessel. The vessels should be heated to about 85 C to about 95 C. Once temperature reaches this level, the oil phase components may be added, including, optionally, anionic emulsifiers if they are oil phase compatible and the carrier oil, as well as any additional oil-phase emulsifiers, antioxidants and/or emollients that may be desired. The temperature should be maintained at this level for about 15 minutes, and the inorganic sunscreen agent added slowly, and the composition mixed for a period of time of at least about 30 minutes. After cooling the pH may then be checked and adjusted if needed. Essential oils may be added later in very small amounts to provide fragrance of most any naturally occurring plant, crop, fruit, or nut. The essential oils are often obtained by simple distillation.

The foregoing examples serve as illustrations of the compositions of this invention, however, they do not limit the scope of the invention described herein.

What is claimed is:

1. A non-endocrine disruptive, cytoprotective sun-block composition consisting of:
    (a) an oil-dispersible inorganic sunscreen compound selected from the group consisting of titanium dioxide, zinc oxide and combinations thereof;
    (b) an emollient which is a cold-pressed aloe barbadensis Miller;
    (c) water;
    (d) stearic acid or a salt thereof;
    (e) a carrier oil which is an essential oil; and
    (f) optionally, (1) additional emollient selected from the group consisting of vegetable oils, silicones and mixtures thereof; (2) butyl-methoxydibenzoylmethane; (3) antioxidant and/or (4) fragrance,
    wherein the carrier oil and the emollient(s) compose from about 2% to about 20% of the total composition weight and the emollient(s) is(are) present in the composition in a ratio to the carrier of from about 1:1 to about 3:1, and
    wherein said composition is capable of protecting skin from harmful effects of sunlight and ultraviolet light.

2. The sun-block composition of claim 1, wherein the cold-pressed aloe barbadensis Miller contains cytoprotective glucose-rich mannose-containing oligosaccharides.

3. The sun-block composition of claim 1, wherein said titanium dioxide has a primary particle size of less than about 300 nm in diameter.

4. The sun-block composition of claim 1, wherein said composition has a pH of at least 5.

5. The sun-block composition of claim 4, wherein said pH is from approximately 6.5 to approximately 8.5.

6. The sun-block composition of claim 1, wherein said composition has a Sun Protection Factor (SPF) of at least 10.

7. A method of protecting mammalian skin from harmful effects of ultraviolet-A and ultraviolet-B radiation and enhancing skin immunocompetency comprising topically applying to skin in need thereof an effective amount of the non-endocrine disruptive, cytoprotective sun-block composition of claim 1.

8. A method of making the non-endocrine disruptive, cytoprotective sun-block composition of claim 1 comprising:
    (a) adding water, cold-pressed aloe, and zinc oxide or titanium dioxide or both in combination to a vessel;
    (b) then adding the oil component;
    (c) then mixing said composition in said vessel.

* * * * *